United States Patent [19]

Weiler

[11] 4,230,704
[45] Oct. 28, 1980

[54] ISOTHIAZOLIDIN-3-ONES

[75] Inventor: Ernest D. Weiler, Ambler, Pa.

[73] Assignee: Rohm and Haas Company, Philadelphia, Pa.

[21] Appl. No.: 31,796

[22] Filed: Apr. 20, 1979

Related U.S. Application Data

[60] Division of Ser. No. 804,971, Jun. 9, 1977, which is a continuation-in-part of Ser. No. 336,650, Feb. 28, 1973, abandoned.

[51] Int. Cl.³ .................... A01N 43/80; C07D 275/02
[52] U.S. Cl. ................................ 424/248.51; 252/106; 252/107; 252/110; 424/256; 424/270; 544/133; 546/209; 548/213
[58] Field of Search ................ 424/270, 248.51, 256

[56] References Cited

U.S. PATENT DOCUMENTS

| | | | |
|---|---|---|---|
| 3,523,121 | 8/1970 | Lewis | 260/306.7 |
| 3,635,997 | 1/1972 | Toepfl | 260/302 |
| 3,761,488 | 9/1973 | Lewis | 260/302 |
| 4,062,859 | 12/1977 | Weiler | 260/302 A |

Primary Examiner—Donald G. Daus
Assistant Examiner—Lisa Jones

[57] ABSTRACT

Isothiazolidin-3-ones of the formula

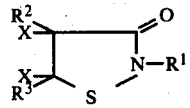

wherein
R¹ is a hydrogen atom, or an alkyl, cycloalkyl, aryl, aralkyl, carbamoyl, or thiocarbamoyl group,
R² and R³ are halogen atoms or alkyl groups, and
X is a halogen atom and compositions containing them are useful in controlling microorganisms, such as bacteria, fungi, algae, and the like.

4 Claims, No Drawings

ISOTHIAZOLIDIN-3-ONES

This is a division of application Ser. No. 804,971 filed June 9, 1977, which in turn is a continuation-in-part application of U.S. application Ser. No. 336,650 filed Feb. 28, 1973 now abandoned.

This invention relates to certain novel isothiazolidin-3-ones, their preparation, biocidal compositions containing them and their utilization in the control of micro-organisms.

The novel isothiazolidin-3-ones of the invention have the formula

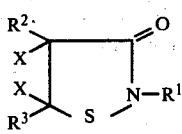

wherein
R is a hydrogen atom, alkyl group, preferably having 1 to 18 carbon atoms, a cycloalkyl group, preferably having a 3 to 6 carbon atom ring and up to 12 carbon atoms, an aralkyl group, preferably having up to 10 carbon atoms, more preferably a phenylalkyl group an aryl group, preferably having up to 10 carbon atoms, more preferably a phenyl group or a carbamoyl group of the formula

wherein
Y is an oxygen or sulfur atom and
$R^4$ is an alkyl group, preferably having 1 to 18 carbon atoms, an alkylsulfonyl group, preferably having 1 to 4 carbon atoms, an arylsulfonyl group, preferably having up to 10 carbon atoms, more preferably a phenylsulfonyl group, an aralkylsulfonyl group, preferably having up to 10 carbon atoms, more preferably a phenylalkylsulfonyl group, an aryl group, preferably having up to 10 carbon atoms, more preferably a phenyl group, an aralkyl group, preferably having up to 10 carbon atoms, more preferably a phenylalkyl group, or a carbalkoxyalkyl group, preferably having up to 4 carbon atoms in each alkyl moiety;
$R^2$ is a halogen atom, preferably a chlorine atom or a bromine atom, or an alkyl group, preferably having 1 to 4 carbon atoms;
$R^3$ is a halogen atom, preferably a chlorine atom or a bromine atom, or an alkyl group, preferably having 1 to 4 carbon atoms; and
X is a halogen atom, preferably a chlorine atom or a bromine atom.

As used in the specification and claims, the term alkyl group is intended to include unsubstituted alkyl groups as well as substituted alkyl groups having up to 18 carbon atoms in which one or more of the hydrogen atoms are replaced by another substituent group. Examples of the substituted alkyl groups which characterize the 3-isothiazolidinones of the invention are hydroxylalkyl, haloalkyl, cyanoalkyl, alkylaminoalkyl, dialkylaminoalkyl, aralkylaminoalkyl, preferably phenylalkylaminoalkyl, arylaminoalkyl, preferably phenylaminoalkyl, carboxyalkyl, carbalkoxyalkyl, alkoxyalkyl, aryloxyalkyl, preferably phenyloxyalkyl, alkylthioalkyl, arylthioalkyl, preferably phenylthioalkyl, isothiazolonylalkyl, haloalkoxyalkyl, carbamoxyalkyl, azacycyloalkylalkyl, such as morpholinoalkyl, piperidinoalkyl, and pyrrolidonylalkyl. Preferably, the total number of carbon atoms in such a substituted alkyl group does not exceed 18, and most preferably, the substituted alkyl group is a substituted ($C_1$-$C_4$) alkyl group. The terms alkenyl group and alkynyl group are intended to define unsubstituted alkenyl and alkynyl groups as well as substituted groups such as haloalkenyl and haloalkynyl.

The term aralkyl group is intended to define unsubstituted aralkyl groups as well as substituted aralkyl groups having one or more of the hydrogen atoms on either the aryl ring or the alkyl chain replaced by another substituent group. Examples of the substituted aralkyl groups which characterize the 3-isothiazolones and the metal salt complexes of the invention are halogen-, nitro-, ($C_1$-$C_4$) alkyl-, or ($C_1$-$C_4$) alkoxy-substituted aralkyl groups.

The term aryl group is intended to define unsubstituted aryl groups, such as phenyl, naphthyl, or pyridyl, as well as such aryl groups having one or more of the hydrogen atoms on the aryl ring replaced by another substituent group. Examples of such substituent groups are halogen, cyano, nitro, ($C_1$-$C_4$) alkyl, ($C_1$-$C_4$) alkoxy, ($C_1$-$C_4$) alkylacylamino, ($C_1$-$C_4$) carbalkoxy and sulfamyl.

Representatives $R^1$ substituents are hydrogen, methyl, ethyl, propyl, butyl, hexyl, octyl, decyl, pentadecyl, octadecyl, cyclopropyl, cyclohexyl, benzyl, phenyl, 4-nitrobenzyl, 3,4-dichlorobenzyl, 4-methoxybenzyl, 4-chlorobenzyl, 4-chlorophenyl, 3,4-dichlorophenyl, 4-methoxyphenyl, 3-methylphenyl, 3,5-dimethylphenyl, 4-nitrophenyl, hydroxymethyl, chloromethyl, chloropropyl, diethylaminoethyl, cyanoethyl, carbomethoxyethyl, ethoxyethyl, 2-methoxy-1-bromoethyl, 3,3,5-trimethylcyclohexyl, phenoxyethyl, 4-chloroanilinomethyl, phenylcarbamoxymethyl, hydroxybutyl, allyl, propynyl, vinyl, carboxyethyl, 1-isothiazolonylethyl, 1,2,2-trichlorovinyl, carbamoyl, thiocarbamoyl, methylcarbamoyl, propylcarbamoyl, octylcarbamoyl, phenylcarbamoyl, 3,4-dichlorophenylcarbamoyl, ethoxyphenylcarbamoyl, nitrophenylcarbamoyl, benzylcarbamoyl, carbethoxymethylcarbamoyl, methylthiocarbamoyl, phenylthiocarbamoyl and methylphenylsulfonylcarbamoyl. Representatives $R^2$ and $R^3$ substituents are bromine, chlorine, iodine, methyl, ethyl, propyl and butyl. The alkyl substituents represented by $R^1$, $R^2$, $R^3$ and $R^4$ can have either branched- or straight-chain spatial configuration.

A preferred embodiment of this invention are the compounds of the formula

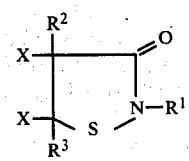

wherein
$R^1$ is
(a) a hydrogen atom;
(b) an unsubstituted alkyl group having 1 to 18 carbon atoms;
(c) a substituted alkyl group having up to 18 carbon atoms which is substituted with one or more substituents selected from the group consisting of hydroxyalkyl, haloalkyl, cyanoalkyl, alkylaminoalkyl, dialkylaminoalkyl, phenylalkylaminoalkyl, phenylaminoalkyl, carboxyalkyl, carbalkoxyalkyl, alkoxyalkyl, phenyloxyalkyl, alkylthioalkyl, phenylthioalkyl, isothiazolonylalkyl, haloalkoxyalkyl, carbamoxyalkyl, morpholinalkyl, piperidinoalkyl and pyrrolidonylalkyl;

(d) a cycloalkyl group having a 3 to 6 carbon atom ring and up to 12 carbon atoms;

(e) an unsubstituted aralkyl group having up to 10 carbon atoms;

(f) a phenylalkyl group having up to 10 carbon atoms wherein one or more of the hydrogen atoms on either the phenyl ring or the alkyl chain is replaced by a substituent selected from the group consisting of halogen, nitro, ($C_1$-$C_4$) alkyl and ($C_1$-$C_4$) alkoxy;

(g) an unsubstituted phenyl or naphthyl group;

(h) a phenyl or naphthyl group which is substituted with one or more substituents selected from the group consisting of halogen, cyano, nitro, ($C_1$-$C_4$) alkyl, ($C_1$-$C_4$) alkoxy, ($C_1$-$C_4$) alkylphenylamino, ($C_1$-$C_4$) carbalkoxy and sulfonyl; or (i) a carbamoyl group of the formula

wherein Y is an oxygen or a sulfur atom and $R^4$ is an unsubstituted alkyl group having 1 to 18 carbon atoms, an alkylsulfonyl group having 1 to 4 carbon atoms, a phenylsulfonyl group having up to 10 carbon atoms, a phenylalkylsulfonyl group having up to 10 carbon atoms, a phenylalkyl group having up to 10 carbon atoms, or a carbalkoxyalkyl group having up to 4 carbon atoms in each alkyl moiety;

$R^2$ is a halogen atom or an unsubstituted ($C_1$-$C_4$) alkyl group;

$R^3$ is a halogen atom or an unsubstituted ($C_1$-$C_4$) alkyl group; and

X is a halogen atom.

Typical compounds of the invention include:
4,4,5,5-tetrachloroisothiazolidin-3-one,
2-methyl-4,4,5,5-tetrachloroisothiazolidin-3-one,
2,4-dimethyl-4,5,5-trichloroisothiazolidin-3-one,
2-ethyl-4,4,5,5-tetrachloroisothiazolidin-3-one,
2-n-octyl-4,4,5,5-tetrachloroisothiazolidin-3-one,
2-n-octadecyl-4,4,5,5-tetrachloroisothiazolidin-3-one,
2,5-dimethyl-4,4,5-trichloroisothiazolidin-3-one,
4,5-dibromo-4,5-dichloro-2-methylisothiazolidin-3-one,
2,5-dimethyl-4,4,5-tribromoisothiazolidin-3-one,
4,5-dichloro-4,5-diiodo-2-methylisothiazolidin-3-one,
2-n-octyl-4,4,5,5-tetrabromoisothiazolidin-3-one,
2-phenyl-4,4,5,5-tetrachloroisothiazolidin-3-one,
2-(4-chlorophenyl)-4,4,5,5-tetrachloroisothiazolidin-3-one,
2-benzyl-5-methyl-4,4,5-tribromoisothiazolidin-3-one,
2-(4-nitrobenzyl)-4,4,5,5-tetrachloroisothiazolidin-3-one,
2-(4-methoxyphenyl)-4-methyl-4,5,5-trichloroisothiazolidin-3-one,
5-ethyl-2-methyl-4,4,5-trichloroisothiazolidin-3-one,
2-(2-bromoethyl)-4,4,5,5-tetrachloroisothiazolidin-3-one,
5-bromo-2-(2-carboxyethyl)-4,4,5-trichloroisothiazolidin-3-one,
2-methoxymethyl-4,4,5,5-tetrachloroisothiazolidin-3-one,
2-(2-hydroxypropyl)-4,4,5,5-tetrabromoisothiazolidin-3-one,
2-(2-dimethylaminoethyl)-4,4,5,5-tetrachloroisothiazolidin-3-one,
2-(2-carbethoxyethyl)-5-methyl-4,4,5-tetrachloroisothiazolidin-3-one,
2-n-butyl-4,4,5,5-tetrachloroisothiazolidin-3-one,
2-n-hexyl-4,4,5,5-tetrachloroisothiazolidin-3-one,
2-n-decyl-4,4,5,5-tetrachloroisothiazolidin-3-one,
2-n-butyl-4-methyl-4,5,5-trichloroisothiazolidin-3-one,
4-methyl-2-n-octyl-4,5,5-trichloroisothiazolidin-3-one,
4-methyl-2-phenyl-4,5,5-trichloroisothiazolidin-3-one,
2-benzyl-4-methyl-4,5,5-trichloroisothiazolidin-3-one,
2-methyl-4,4,5,5-tetrabromoisothiazolidin-3-one,
2-N-methylcarbamoyl-4,4,5,5-tetrachloroisothiazolidin-3-one,
2-N-ethylthiocarbamoyl-4,4,5,5-tetrachloroisothiazolidin-3-one,
2-N(3-chlorophenyl) carbamoyl-4,4,5,5-tetrachloroisothiazolidin-3-one,
2(3-chlorophenyl)-4,4,5,5-tetrachloroisothiazolidin-3-one,
2-(2-carbomethoxyethyl)-4,4,5,5-tetrachloroisothiazolidin-3-one,
2-(4-chloroanilinomethyl)4,4,5,5-tetrachloroisothiazolidin-3-one,
2-morpholinomethyl-4,4,5,5-tetrachloroisothiazolidin-3-one,
2-phenylcarbamoxymethyl-4,4,5,5-tetrachloroisothiazolidin-3-one,
2-chloromethyl-4,4,5,5-tetrachloroisothiazolidin-3-one,
5-methyl-4,4,5-trichloroisothiazolidin-3-one,
4-methyl-4,5,5-trichloroisothiazolidin-3-one,
5-bromo-4,4,5-trichloroisothiazolidin-3-one,
4-bromo-4,5,5-trichloroisothiazolidin-3-one, and the like.

In a preferred embodiment of the invention, $R^1$ is an unsubstituted alkyl group of 1 to 18 carbon atoms, X is chlorine, and $R^2$ and $R^3$ are methyl or chlorine.

All of the isothiazolidin-3-ones of the invention can be prepared by halogenation of a 4-isothiazolin-3-one of the formula

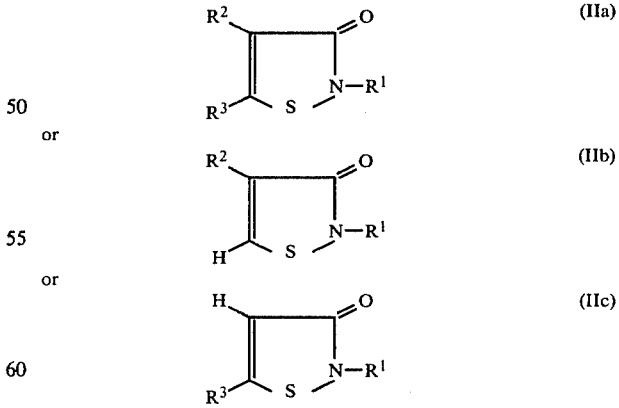

wherein $R^1$, $R^2$ and $R^3$ are as defined above. The preparation and properties of the 4-isothiazolin-3-ones from which isothiazolinidin-3-ones of the invention are made are described in U.S. Pat. No. 3,523,121, of Lewis, et al., granted Aug. 4, 1970, and U.S. patent applications Ser. No. 836,660, filed on June 25, 1969, by S. N. Lewis, et al., and Ser. No. 855,046, filed Sept. 3, 1969, by S. N. Lewis, et al.

The halogenation reaction can be carried out over a broad temperature range, preferably about −15° to about 120° C., most preferably about 25° to about 70° C. Generally, nonhydroxylic solvents, such as ethyl acetate, butyl acetate, dimethylformamide, acetone, and the like are used. An excess of the halogenating agent can be employed if desired. The product of the halogenation reaction can be isolated by any convenient technique, such as distillation, extraction, chromatography, or the like. Among the suitable halogenating agents for making the compounds of the invention are bromine, chlorine, iodine, sulfuryl bromide, sulfuryl chloride, iodine monochloride, iodine monobromide, and the like. Chlorine and bromine are the preferred halogenating agents.

Those isothiazolidin-3-ones of the invention in which $R^2$ is a methyl group can also be prepared by the cyclization of a dithiodiisobutyramide of the formula

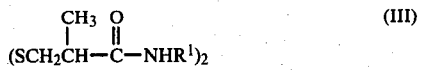

wherein $R^1$ is as defined above. The cyclization is generally carried out by the simultaneous addition of a halogenating agent, such as chlorine, and the amide to a solvent, such as ethylacetate, butylacetate, acetone, dimethylformamide, or the like. The cyclization reaction is preferably carried out at a temperature of about 25° to about 70° C. The isothiazolidin-3-one can be isolated from the reaction mixture by any suitable procedure.

The following examples are set forth to illustrate further this invention but are not intended to limit it in any way. Table I sets forth typical isothiazolidin-3-ones of the invention prepared as described above, along with their elemental analyses and melting points or boiling ranges. Specific illustrative preparations of the compounds of Examples 1, 7, 8, 12, and 14 are described after Table I. All temperatures are in degrees Centigrade and percentages by weight unless otherwise stated.

EXAMPLE 1

Preparation of 2,4-Dimethyl-4,5,5-trichloroisothiazolidin-3-one

Method A

To 100 ml. of ethyl acetate at 0° are added simultaneously over 1 hour, 26.4 g (0.1 mole) of N,N'-dimethyl-3,3'-dithiodiisobutyramide in 40 equal portions at 1.5 minute intervals, and 29 g (0.41 mole) of chlorine. The temperature is maintained between −5° and 0° during the addition. The mixture is allowed to warm to room temperature and filtered to remove suspended solid. The filtrate is washed with dilute aqueous sodium bicarbonate until neutral. The solution is dried over anhydrous magnesium sulfate and evaporated leaving a yellow-orange oil. The oil is distilled; b.p. 59°-61° C./0.15 mm. The distillate, 9.95 g, is shown by thin layer chromatography (TLC) (silica/methylene chloride) to contain two components. Approximately 3 g of this material is chromatographed on a silica dry column developed with methylene chloride. The column is divided in three equal portions. Extraction with ether of the portion nearest the solvent front, followed by evaporation of the extract, gives 1.31 g (19%) of colorless oil, which solidifies to a white solid, 2,4-dimethyl-4,5,5-trichloroisothiazolidin-3-one, m.p. 46.5°-48° C.

Method B

To a solution of 5.92 g (0.0459 mole) of 2,4-dimethyl-4-isothiazolin-3-one in 20 ml of ethyl acetate at room temperature is added over ½ hour, 10.4 g (0.147 mole) of chlorine. White solid precipitates while the temperature rises to a high of about 67° and slowly drops. The solid redissolves by the end of chlorine addition. The solution is degassed and evaporated under reduced pressure leaving 10.6 of yellow oil which solidifies on standing. Crystallization of the solid from heptane gives 7.3 g (68%) of 2,4-dimethyl-4,5,5-trichloroisothiazolidin-3-one, m.p. 43°-45° C.

EXAMPLE 7

Preparation of 4-Methyl-2-phenyl-4,5,5-trichloroisothiazolidin-3-one

TABLE I

ISOTHIAZOLIDIN-3-ONES

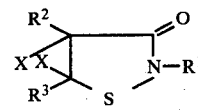

| Ex. No. | $R^1$ | $R^2$ | $R^3$ | X | mp/bp°C. (mn) | Emp. Form. | C | H | N | S | Cl |
|---|---|---|---|---|---|---|---|---|---|---|---|
| 1 | CH$_3$ | CH$_3$ | Cl | Cl | 46–43 | C$_6$H$_5$Cl$_3$NOS | 25.78(25.59) | 2.49(2.56) | 4.47(5.97) | 13.53(13.65) | 45.36(45.48) |
| 2 | C$_8$H$_{17}$-n | CH$_3$ | Cl | Cl | 134–136/0.15 | C$_{12}$H$_{20}$Cl$_3$NOS | 44.30(43.30) | 6.08(6.06) | 4.23(4.21) | 9.93(9.64) | 30.35(31.37) |
| 3 | C$_2$H$_{17}$-n | Cl | Cl | Cl | 138–142/0.15 | C$_{11}$H$_{17}$Cl$_4$NOS | 37.93(37.41) | 4.86(4.85) | 3.91(3.96) | 8.96(9.08) | 39.66(40.15) |
| 4 | C$_4$H$_9$-n | CH$_3$ | Cl | Cl | 88.98/0.20 | C$_8$H$_{12}$Cl$_3$NOS | 35.18(34.72) | 4.39(4.34) | 5.14(5.06) | 11.35(11.57) | 37.67(18.52) |
| 5 | CH$_2$C$_6$H$_5$ | CH$_3$ | Cl | Cl | 138–142/0.30 | C$_{11}$H$_{10}$Cl$_3$NOS | 43.02(42.51) | 3.11(3.22) | 4.46(4.51) | 10.07(10.31) | 33.71(34.30) |
| 6 | CH(CH$_3$)$_2$C$_5$H | CH$_3$ | Cl | Cl | 85–93/0.60 | C$_8$H$_{12}$Cl$_3$NOS | 35.39(34.72) | 4.60(4.34) | 5.09(5.06) | 11.30(11.57) | 37.36(38.52) |
| 7 | C$_6$H$_5$ | CH$_3$ | Cl | Cl | 79–81 | C$_{10}$H$_8$Cl$_3$NOS | 39.47(40.47) | 2.64(2.70) | 4.41(4.72) | 10.11(10.79) | 38.04(35.72) |
| 8 | CH$_3$ | Cl | Cl | Cl | 52–55 | C$_4$H$_3$Cl$_4$NOS | 19.01(18.82) | 1.00(1.18) | 5.35(5.49) | 12.61(12.55) | 55.80(55.69) |
| 9 | C$_6$H$_{13}$—n | Cl | Cl | Cl | 128–140/0.30 | C$_9$H$_{13}$Cl$_4$NOS | 33.48(33.23) | 3.76(4.00) | 4.10(4.31) | 9.59(9.58) | 43.62(43.69) |
| 10 | C$_2$H$_5$ | Cl | Cl | Cl | 55–56 | C$_5$H$_5$Cl$_4$NOS | 22.91(22.30) | 2.01(1.86) | 5.23(5.20) | 11.70(11.90) | 52.15(52.79) |
| 11 | C$_6$H$_{11}$-cyclo | Cl | Cl | Cl | 69–71 | C$_9$H$_{11}$Cl$_4$NOS | 34.90(33.44) | 3.64(3.41) | 4.47(4.33) | 10.08(9.91) | 41.67(18.96) |
| 12 | C$_4$H$_9$-n | Cl | Cl | Cl | 102–107/0.4 | C$_7$H$_9$Cl$_4$NOS | 28.28(28.28) | 3.16(3.03) | 4.74(4.71) | 10.79(10.77) | 47.96(47.81) |
| 13 | C$_{10}$H$_{21}$-n | Cl | Cl | Cl | 165–173/0.4 | C$_{13}$H$_{21}$Cl$_4$NOS | 42.14(40.94) | 5.45(5.51) | 3.53(3.67) | 12.91(10.32) | 34.99(37.27) |
| 14 | CH$_2$C$_6$H$_5$ | Cl | Cl | Cl | 142–143/0.35 | C$_{10}$H$_7$Cl$_4$NOS | 36.30(36.25) | 2.23(2.11) | 4.22(4.23) | 9.59(9.67) | 42.61(42.90) |
| 15 | C$_6$H$_5$ | Cl | Cl | Cl | 92–95 | C$_9$H$_5$Cl$_4$NOS | 33.56(34.07) | 1.86(1.58) | 4.17(4.42) | 9.91(10.09) | 45.66(44.79) |
| 16 | CH(CH$_3$)C$_6$H$_5$ | Cl | Cl | Cl | 148–155/0.35 | C$_{11}$H$_9$Cl$_4$NOS | 39.17(38.26) | 2.71(2.61) | 4.01(4.06) | 5.11(9.30) | 38.95(41.16) |
| 17 | C$_6$H$_4$Cl-3 | Cl | Cl | Cl | 83–85.5 | C$_9$H$_4$Cl$_5$NOS | 31.49(30.72) | 1.37(1.14) | 3.84(3.98) | 9.34(9.10) | 43.74(56.50) |

To a solution of 11.27 g (0.05 mole) of crude 5-chloro-4-methyl-2-phenyl-4-isothiazolin-3-one in 100 ml. of ethyl acetate is added over 15 minutes 3.55 g (0.05 mole) of chlorine. During chlorine addition the temperature rises to about 37°. After cooling to room temperature the solution is evaporated to 14.0 g of dark amber oil. A TLC of this oil (silica/toluene) shows that it contains at least six components. The oil is dry-column chromatographed on silica with toluene, and the leading third of the column is extracted with ether. The extract is concentrated and dried to give 3.31 g of yellow solid. Recrystallization from ether gives 1.1 g (7.6%) of yellow tan solid, 4-methyl-2-phenyl-4,5,5-trichloroisothiazolidin-3-one, m.p. 52°–55° C.

EXAMPLE 8

Preparation of 2-Methyl-4,4,5,5-tetrachloroisothiazolidin-3-one

Method A

To a suspension of 37.2 g (0.2 mole) of 5-chloro-2-methyl-4-isothiazolin-3-one hydrochloride in 100 ml. of ethyl acetate is added 100 ml. of N,N-dimethylformamide. To this mixture is added over ½ hour, 28.4 g (0.4 mole) of chlorine. The temperature rises but is maintained below 35° by external cooling. All solid dissolves after about 5 minutes. When the chlorine addition is complete, the mixture is cooled to 0° causing separation of 14.2 g of 4,5-dichloro-2-methyl-4-isothiazolin-3-one. The filtrate is concentrated under reduced pressure to remove ethyl acetate and dimethylformamide. Dilution of the concentrate with water causes separation of an oil which solidifies on standing. The solid, 19.71 g, is chromatographed on a silica dry-column developed with benzene. The leading half of the column is extracted with benzene. Concentration of the extract gives 8.5 g (17%) of 2-methyl-4,4,5,5-tetrachloroisothiazolidin-3-one, m.p. 79.5°–81.5° C.

Method B

To a suspension of 30.3 g (0.2 mole) of pure and dry 2-methyl-4-isothiazolin-3-one hydrochloride in 200 ml. of ethyl acetate is added over 1 hour, 71 g (1 mole) of chlorine. The reaction exotherms to 55° C. in ½ hour and all solid is dissolved after about ¾ hour. The solution is degassed and evaporated under reduced pressure to give a cream color mush. The mush is shown by TLC (silica/toluene) to contain two major components. Crystallization of the mush from methanol gives 16.8 g of 4,5-dichloro-2-methyl-4-isothiazolin-3-one. Evaporation of the filtrate gives 23.4 of material which is chromatographed on a silica dry column with toluene. The fraction close to the solvent front is extracted and gives 8.8 g of crude product. Recrystallization from methanol gives 6.55 g (13%) of white crystalline 2-methyl-4,4,5,5-tetrachloroisothiazolidin-3-one, m.p. 77°–80° C.

EXAMPLE 12

Preparation of 2-n-Butyl-4,4,5,5-tetrachloroisothiazolidin-3-one

To a solution of 15.7 g (0.1 mole) of 2-n-butyl-4-isothiazolin-3-one in 100 ml. of ethyl acetate is added, over ½ hour, 21.3 g (0.3 mole) of chlorine. The temperature rises to a high of about 62° during which solid first separates and then redissolves. The solution is concentrated under reduced pressure to give 26.56 g of yellow oil. A TLC (silica/toluene) shows two major components. The oil is then chromatographed on a silica dry-column with toluene. Extraction of the leading half of the column with ether followed by evaporation gives 8.87 g of crude product. Distillation provides 8.13 g (27%) of pure 2-n-butyl-4,4,5,5-tetrachloroisothiazolidin-3-one, b.p. 102–107/0.4 mm °C.

EXAMPLE 14

Preparation of 2-Benzyl-4,4,5,5-tetrachloroisothiazolidin-3-one

The procedure of Example 12 is followed using 18.9 g (0.1 mole) of 2-benzyl-4-isothiazolin-3-one in 100 ml. of ethyl acetate and 21.3 g (0.3 mole) of chlorine added in ½ hour. The reaction exotherms to about 68° C. Evaporation of the reaction solution gives an orange oil. The oil is chromatographed on a silica dry-column with toluene. The leading half of the column is extracted with ether and evaporated to yield 8.3 g of crude product. Distillation gives 7.2 g (22%) of pure 2-benzyl-4,4,5,5-tetrachloroisothiazolidin-3-one, b.p. 142–143/0.35 mm °C.

The novel isothiazolidinones of the invention are biocidally active compounds, which are particularly useful for the control of microorganisms. For example, the isothiazolidinones are especially effective as bactericidal, algaecidal, fungicidal, and slimicidal agents. Furthermore, these novel compounds have generally demonstrated unexpectedly fast speed-of-kill against undesirable microorganisms.

Antibacterial and fungicidal activity are evaluated by the Serial Dilution Test (Broth Titer Test) wherein a series of broths containing varying dilutions of a test compound and an organism are halved starting with a dilution of 1:1000. The values obtained, which are summarized in Table II, represent the maximum dilution in parts per million by weight at which the compound under evaluation renders complete control of the organism. *Staphylococcus aureus* (Staph.), *Escherichia coli* (*E. coli*) and *Pseudomonas aeruginosa* (Pseud.) were the bacterial organisms employed in this test, and the fungi employed were *Aspergillus niger* (*A. niger*) and *Rhizopus stolonifer* (*Rhiz.*)

TABLE II

| | Serial Dilution Data, Endpoint (ppm) | | |
|---|---|---|---|
| Example No. | Bacteria E. coli./Staph. | Pseud. | Fungi A. niger/Rhiz. |
| 1 | 125 | 63 | 125 |
| 2 | 125 | 125 | 63 |
| 3 | 125 | 63 | 32 |
| 4 | 125 | 125 | 125–500 |
| 5 | 125 | 63 | 63 |
| 6 | 125 | 125 | 125 |
| 7 | 125 | 125 | 125 |
| 8 | 125 | 63 | 125 |
| 9 | 125 | 63 | 63 |
| 10 | 63 | 125 | 63 |
| 11 | 125 | 125 | 63 |
| 12 | 125 | 125 | 63 |
| 13 | >125 | 125 | 125 |
| 14 | >125 | >125 | 125 |
| 15 | >125 | >125 | >125 |
| 16 | >125 | 125 | 125 |

The isothiazolidinones of the invention are also effective as plant bactericides and plant fungicides. Among the phytopathogenic bacteria and fungi which are controlled by compounds of the invention are bean powdery mildew (*Erysiphe polygoni*), rice blast (*Piricularia oryzae*), tomato late blight (*Phytophthora infestans*), cereal rust (*Puccinia recondita*), downy mildew (*Plasmooara viticola*), and bacterial leaf spot (*Xanthomonas vesicatoria*). When used as plant bactericides or fungicides, the isothiazolidinones are generally applied at a rate of about 0.1 to about 25 pounds per acre, and preferably about 0.25 to about 10 pounds per acre. The rate of application is usually dependent on the isothiazolidinone used, the phytopathogenic organism to be controlled, the method and type of application, and other similar factors.

Generally, control of a living organism is achieved in accordance with this invention by contacting the organism with an isothiazolidinone in an amount which is effective to control the organism. Any of the techniques known in the art can be employed to disseminate the isothiazolidinones in a manner so as to achieve the desired contact with the organism to be controlled.

The compounds of this invention can be readily utilized as slimicides, algaecides, bactericides, and fungicides in any locus and particularly in aqueous media, such as, for example, water-cooling systems, swimming pools, paper pulp processes, aqueous polymer dispersions, water-based paints, and the like. In addition, these compounds and compositions containing them can function as, for example, fabric and leather preservatives, cosmetic preservatives, soap additives, sanitizing agents, such as in laundry soaps and detergents, preservatives for metal working compounds, such as emulsifiable cutting oils, preservatives for fuels, fiber spin finish biocides, and the like.

The isothiazolidinones of the invention are also useful as laundry sanitizing agents, in which fast speed of-kill is particularly advantageous. Generally, about 0.01 to about 10% by weight and preferably about 0.05 to about 5% by weight, of the isothiazolidinone will be added to a soap or detergent to make a sanitizing laundry composition. Isothiazolidinones can also be added directly to the laundry wash water, generally at a concentration of about 0.5 to about 1000 parts per million by weight.

In general, a locus subject to contamination by microorganisms can be protected in accordance with this invention by incorporating into the locus an isothiazolidino in an amount which is effective to control the microorganism. The term "contamination" is meant to include attack by micro organisms which leads to a chemical or physical breakdown or disintegration of the locus as well as proliferation of the microorganisms within the locus without an accompanying deleterious effect. The exact amount of isothiazolidinone required will, of course, vary with the medium being protected, the microorganisms being controlled, the particular isothiazolidinones or compositions containing the isothiazolidinones being employed, the degree of control desired, and other factors. Typically, in a liquid medium suitable control is obtained when the isothiazolidinones are incorporated in the range of 0.1 to 10,000 parts per million (ppm) or 0.00001 to 1% based on the weight of the medium. A range of 1 to 2000 ppm is preferred.

The term "control" as employed in the specification and claims of this application is to be construed as the effect of any means which adversely affects the existence or growth of any living organism or microorganism. This effect may comprise complete killing action, eradication, arresting in growth, inhibition, reduction in number or any combination of these effects.

The isothiazolidinones of the invention are also useful as paint preservatives and paint fungistats. Microbial activity in water-based and oil-based paint emulsions is inhibited when the isothiazolidinones are incorporated into the paint. The isothiazolidinones are also mildewcides for paint films when incorporated in paint formulations.

The isothiazolidinones of this invention are especially useful as agricultural bactericides and fungicides. As such, they are particularly valuable when formulated in bactericidal and fungicidal compositions. Such compositions normally comprise an agronomically acceptable carrier and an isothiazolidinone or mixture of isothiazolidinones as the active agent. Where necessary or desirable, surfactants or other additives may be incorporated to give uniformly formulated mixtures. By "agronomically acceptable carrier" is meant any substance which can be utilized to dissolve, dispense, or diffuse the chemical incorporated therein without impairing the effectiveness of the toxic agent and which does no permanent damage to the environment, soil, equipment, or agronomic crops.

For use as pesticides, the compounds of this invention are usually taken up in an agronomically acceptable carrier or formulated so as to render them suitable for subsequent dissemination. For example, the isothiazolidinones can be formulated as wettable powders, emulsion concentrates, dusts, granular formulations, aerosol or flowable emulsifiable concentrates. In such formulations the isothiazolidinones are extended with a liquid or solid carrier and, when desired, suitable surfactants are incorporated.

Compounds of this invention can be dissolved in a water-miscible liquid, such as ethanol, isopropanol, acetone, and the like. Such solutions are easily extended with water.

The isothiazolidinones can be taken up on or mixed with a finely particled solid carrier, as for example, clays, inorganic silicates, carbonates, and silicas. Organic carriers can also be employed. Dust concentrates are commonly made wherein isothiazolidones are present in the range of 20 to 80%. For ultimate applications, these concentrates are normally extended with additional solid from about 1 to 20%.

Wettable powder formulations are made by incorporating the compounds of this invention in an inert, finely divided solid carrier along with a surfactant which may be one or more emulsifying, wetting, dispersing or spreading agents or blend of these. The isothiazolidinone are usually present in the range of 10 to 80% by weight an the surfactants in from 0.5 to 10% by weight. Commonly-used emulsifying and wetting agents include polyoxyethylated derivatives of alkylphenols, fatty alcohols, fatty acids, and alkylamines, alkylarene sulfonates and dialkyl sulfosuccinates. Spreading agents include such materials as glycerol mannitan laurate and a condensate of polyglyce and oleic acid modified with phthalic anhydride. Dispersing agents include such materials as the sodium salt of the copolymer of maleic anhydride and an olefin such as diisobutylene, sodium lignin sulfonate and sodium formaldehyde-naphthalene sulfonates.

One convenient method for preparing a solid formulation is to impregnate the isothiazolidinone toxicant onto the solid carrier by means of a volatile solvent, such as acetone. In this manner adjuvants, such as activators, adhesives, plant nutrients, synergists and various surfactants, can also be incorporated.

Emulsifiable concentrate formulations can be prepared by dissolving the isothiazolidinones of this invention in an agronomically acceptable organic solvent and adding a solvent-soluble emulsifying agent. Suitable solvents are usually water-immiscible and may be found in the hydrocarbon, chlorinated hydrocarbon, ketone, ester, alcohol and amide classes of organic solvents. Mixtures of solvents are commonly employed. The surfactants useful as emulsifying agents may constitute about 0.5 to 10% by weight of the emulsifiable concentrate and may be anionic, cationic or non-ionic in character. Anionic surfactants include alcohol sulfates or sulfonates, alkylarene sulfonates and sulfosuccinates. Cationic surfactants include fatty acid alkylamine salts and fatty acid alkyl quaternaries. Non-ionic emulsifying agents include alkylene oxide adducts of alkylphenols, fatty alcohols, mercaptans and fatty acids. The concentration of the active ingredients may vary from 10 to 80%, preferably in the range of 25 to 50%.

For use as phytopathogenic agents, these compounds should be applied in an effective amount sufficient to exert the desired biocidal activity by techniques well known in the art. Usually, this will involve the application of the isothiazolidinones to the locus to be protected in kyl, alkoxyalkyl, phenyloxyalkyl, alkylthioalkyl, phenylthioalkyl, isothiazolonylalkyl, and haloalkoxyalkyl, carbamoxyalkyl, morpholinalkyl, piperidinoalkyl and pyrrolidonylalkyl;
(d) cycloalkyl group having a 3 to 6 carbon atom ring and up to 12 carbon atoms;
(e) an unsubstituted aralkyl group having up to 10 carbon atoms;
(f) a phenylalkyl group having up to 10 carbon atoms wherein one of the hydrogen atoms on either the phenyl group or the alkyl chain is replaced by a substituent selected from the group consisting of halogen, nitro, $(C_1-C_4)$ alkyl and $(C_1-C_4)$ alkoxy;
(g) an unsubstituted phenyl or naphthyl group;
(h) a phenyl or naphthyl group which is substituted with one substituent selected from the group consisting of halogen, cyano, nitro, $(C_1-C_4)$ alkyl, $(C_1-C_4)$ alkoxy, $(C_1-C_4)$ alkylphenylamino, $(C_1C_4)$ carbalkoxy and sulfonyl; or
(i) a carbamoyl group of the formula

wherein Y is an oxygen or a sulfur atom and $R^4$ is an unsubstituted alkyl group having 1 to 18 carbon atoms, an alkylsulfonyl group having 1 to 4 carbon atoms, a phenylsulfonyl group having up to 10 carbon atoms, a phenylalkylsulfonyl group having up to 10 carbon atoms, a phenylalkyl group having up to 10 carbon atoms, or a carbalkoxyalkyl group having up to 4 carbon atoms in each alkyl moiety;

$R^2$ is a halogen atom or an unsubstituted $(C_1-C_4)$ alkyl group;

$R^3$ is a halogen atom or an unsubstituted $(C_1-C_4)$ alkyl group; and

X is a halogen atom.

3. A method according to claim 2 wherein the microorganisms are bacteria or fungi.

4. A method according to claim 3 wherein the microorganisms are phytopathogenic bacteria or fungi.

* * * * *